(12) United States Patent
Moore

(10) Patent No.: US 11,311,682 B2
(45) Date of Patent: *Apr. 26, 2022

(54) CAP ASSEMBLY FOR MEDICAMENT DELIVERY DEVICE

(71) Applicant: SHL MEDICAL AG, Zug (CH)

(72) Inventor: Andrew Moore, Ft. Lauderdale, FL (US)

(73) Assignee: SHL MEDICAL AG, Zug (CH)

( * ) Notice: Subject to any disclaimer, the term of this patent is extended or adjusted under 35 U.S.C. 154(b) by 418 days.

This patent is subject to a terminal disclaimer.

(21) Appl. No.: 16/516,095

(22) Filed: Jul. 18, 2019

(65) Prior Publication Data

US 2019/0336701 A1 Nov. 7, 2019

Related U.S. Application Data

(63) Continuation of application No. 15/182,893, filed on Jun. 15, 2016, now Pat. No. 10,363,378.

(51) Int. Cl.
*A61M 5/32* (2006.01)
*A61M 5/20* (2006.01)

(52) U.S. Cl.
CPC ............ *A61M 5/3213* (2013.01); *A61M 5/20* (2013.01); *A61M 5/3202* (2013.01);
(Continued)

(58) Field of Classification Search
CPC .... A61M 5/3213; A61M 5/20; A61M 5/3202; A61M 5/3204; A61M 5/3243; A61M 5/326; A61M 2207/00
See application file for complete search history.

(56) References Cited

U.S. PATENT DOCUMENTS 9,333,305 B2  5/2016 McLoughlin et al.
9,522,233 B2  12/2016 Bicknell et al.
(Continued)

FOREIGN PATENT DOCUMENTS

CN  101945679 A  1/2011
CN  102781500 A  11/2012
(Continued)

OTHER PUBLICATIONS

Extended European Search Report Issued in European Application No. 17173242.3 dated Nov. 17, 2016.
(Continued)

*Primary Examiner* — Lauren P Farrar
(74) *Attorney, Agent, or Firm* — McDonnell Boehnen Hulbert & Berghoff LLP

(57) ABSTRACT

The present disclosure relates to a cap assembly for a medicament delivery device. The cap assembly comprises: a cap body arranged to be mounted to a proximal end of a medicament delivery device for protecting and for removing a medicament delivery member shield. The cap body has an inner cap structure defining a channel extending along the central axis of the cap body, and a gripping member configured to be received in the channel. The gripping member is radially flexible and has a first leg, a second leg, and a connecting portion extending between the first leg and the second leg. The first leg and the second leg each has a proximal portion that is radially flexible and extends distally from the connecting portion. Each proximal portion has an inclined section extending radially inwards in an axial direction away from the connecting portion. Each of the first leg and the second leg has a distal portion extending from the inclined section, the distal portions being radially flexible and extending radially outwards in an axial direction away from the proximal portions to allow the gripping
(Continued)

member to receive a medicament delivery member shield between the distal portions. The gripping member and an inner wall of the channel are configured to engage to retain the gripping member in the inner cap structure. Each distal portion is provided with a medicament delivery member shield gripper configured to engage with a medicament delivery member shield when the gripping member engages with the inner wall of the channel and the gripping member has received a medicament delivery member shield causing the proximal portions and the distal portions to flex radially inwards.

20 Claims, 3 Drawing Sheets

(52) U.S. Cl.
CPC .......... *A61M 5/3204* (2013.01); *A61M 5/326* (2013.01); *A61M 5/3243* (2013.01); *A61M 2207/00* (2013.01)

(56) References Cited

U.S. PATENT DOCUMENTS

| | | | |
|---|---|---|---|
| 9,656,026 | B2 | 5/2017 | Bostrom |
| 10,092,703 | B2 | 10/2018 | Mounce et al. |
| 2003/0212370 | A1 | 11/2003 | Barrelie |
| 2013/0150801 | A1 | 6/2013 | Ekman |
| 2014/0243753 | A1* | 8/2014 | Bostrom ............. A61M 5/3213 604/198 |
| 2015/0335826 | A1 | 11/2015 | Huet |
| 2016/0144132 | A1 | 5/2016 | Scanlon |

FOREIGN PATENT DOCUMENTS

| | | |
|---|---|---|
| CN | 103764207 A | 4/2014 |
| CN | 104428021 A | 3/2015 |
| CN | 104771815 A | 7/2015 |
| EP | 3257540 A1 | 12/2017 |
| TW | 21004665 A1 | 2/2010 |
| TW | 201315504 A1 | 4/2013 |
| TW | 201509461 A | 3/2015 |
| TW | 201509474 A | 3/2015 |
| WO | 2009081103 A1 | 7/2009 |
| WO | 2010/089589 A1 | 8/2010 |
| WO | 2010089589 A1 | 8/2010 |
| WO | 2014139939 A1 | 9/2014 |
| WO | 2015110532 A1 | 7/2015 |
| WO | 2015144871 A1 | 10/2015 |

OTHER PUBLICATIONS

Search Report issued in Taiwanese Patent Application No. 106118720 dated Mar. 6, 2018.

* cited by examiner

ND DELIVERY DEVICE

CAP ASSEMBLY FOR MEDICAMENT DELIVERY DEVICE

CROSS-REFERENCE TO RELATED APPLICATION

This application is a continuation of U.S. application Ser. No. 15/182,893, filed Jun. 15, 2016, which is hereby incorporated by reference in its entirety.

TECHNICAL FIELD

The present disclosure generally relates to medical devices. In particular, it relates to a cap assembly for a medicament delivery device, to a medicament delivery device comprising the same, and to a method of assembling a medicament delivery device.

BACKGROUND

Medicament delivery devices, such as injectors and inhalers, typically comprise a housing in which a medicament container containing a medicament is to be arranged. Upon activation of the medicament delivery device, the medicament is expelled through a medicament delivery member, for example a needle or a nozzle.

In order to protect and to keep the medicament delivery member sterile, the medicament delivery member may be provided with a medicament delivery member shield, or sheath, such as a Flexible Needle Shield (FNS) or a Rigid Needle Shield (RNS). The medicament delivery member shield may thus be attached to the medicament container to cover the medicament delivery member, during assembly of the medicament container or of the medicament delivery device.

Moreover, the medicament delivery device may comprise a removable cap which is mounted to the proximal end of the housing, i.e. that end which is placed towards the injection site during medicament delivery, of the medicament delivery device, or to the proximal end of the medicament container. The removable cap has the function of providing mechanical protection of the medicament delivery member while attached to the housing or medicament container, and to remove the medicament delivery member shield when the cap is removed from the housing.

WO2015/144871 A1 discloses a sheath removal mechanism for removing a protective needle sheath from a medicament from a medicament container that is to be arranged in a medicament delivery device. The sheath removal mechanism comprises a cap attachable to a proximal end of the medicament delivery device. The cap comprises at least one ledge adapted to engage the protective needle sheath, and has a proximal opening. An assembly tool can be provided into the proximal opening from the front side of the cap to splay sheath removal beams on the inner side of the cap apart such that the protective needle sheath may be received between the sheath removal beams. By removing the assembly tool, the beams will no longer be splayed, and the ledge will thereby engage the protective needle sheath.

SUMMARY

According to WO2015/144871 A1, an assembly tool has to be used to splay the sheath removal beams apart so that the cap may receive the protective needle sheath. The assembly procedure of the cap with the protective needle sheath is hence rather complex.

In view of the above, a general object of the present disclosure is to provide a cap assembly which simplifies assembly of a medicament delivery device.

There is hence according to a first aspect of the present disclosure provided a cap assembly for a medicament delivery device, the cap assembly comprising a cap body arranged to be mounted to a proximal end of a medicament delivery device for protecting and for removing a medicament delivery member shield, which cap body has an inner cap structure defining a channel extending along the central axis of the cap body, and a gripping member configured to be received in the channel with a friction fit and to receive a medicament delivery member shield, wherein the gripping member has a first leg, a second leg, and a connecting portion extending between the first leg and the second leg, which connecting portion defines a leading edge of the gripping member when received by the channel, the first leg and the second leg having a respective proximal portion that are radially flexible and extending distally from the connecting portion, each proximal portion having an inclined section extending radially inwards in an axial direction away from the connecting portion, and a respective distal portion extending from the inclined section, the distal portions being radially flexible and extending radially outwards in an axial direction away from the proximal portions to allow the gripping member to receive a medicament delivery member shield between the distal portions, the gripping member and an inner wall of the channel being configured to engage to retain the gripping member in the inner cap structure, and each distal portion being provided with a medicament delivery member shield gripper configured to engage with a medicament delivery member shield when the gripping member engages with the inner wall of the channel and the gripping member has received a medicament delivery member shield causing the proximal portions and the distal portions to flex radially inwards.

The gripping member is placed in the channel of the inner cap structure during assembly. Therefore no additional special tool is necessary for the assembly procedure of the cap with the medicament delivery member shield. Once the gripping member has been properly installed in the channel, engaging therewith, the medicament delivery member shield may be inserted between the first and second legs of the gripping member and into the channel by bringing the two components together, especially since the distal portions extend radially outwards in a distal direction along the central axis of the gripping member. The oppositely inclined configuration of the proximal portions and the distal portions, and the dimensioning between the oppositely arranged first leg and second leg ensures that when the medicament delivery member shield is pushed in between the first leg and the second leg maximally into the gripping member, the proximal portion and the distal portion will expand radially. The medicament delivery member shield grippers will as a result be moved radially inwards and engage with the medicament delivery member shield if the gripping member is arranged in the channel, which delimits radial outwards expansion of the first leg and the second leg. Assembly of a medicament delivery device comprising a cap and medicament delivery member shield may hence be facilitated.

According to one embodiment the configuration of the inclined sections and the distal portions form a waist of the gripping member.

According to one embodiment each distal portion has a straight extension from the corresponding inclined section to the medicament delivery member shield gripper.

According to one embodiment each medicament delivery member shield gripper extends radially inwards.

According to one embodiment each medicament delivery member shield gripper is formed by a radially inwardly curved end portion of the corresponding distal portion.

According to one embodiment the channel has opposing inner walls that extend in parallel in the longitudinal direction of the cap body.

According to one embodiment the opposing inner walls extend in parallel with each other along the entire extension of the channel.

According to one embodiment the gripping member is made of metal.

According to one embodiment the gripping member and the inner wall of the channel are configured to engage when the gripping member is maximally received in the channel.

According to one embodiment the connecting portion has a radial protrusion and the channel has at least one recess for receiving the radial protrusions for locking the gripping member in the maximally received position.

According to one embodiment the connecting portion has a cylindrical section, wherein the radial protrusion extends circumferentially along an external surface of the cylindrical section, and wherein the at least one recess extends circumferentially along an inner surface of the channel.

There is according to a second aspect of the present disclosure provided a medicament delivery device comprising: a housing arranged to receive a medicament container and a medicament delivery member shield, which housing has a proximal end and a distal end, and a cap assembly according to the first aspect, configured to cover the proximal end of the housing.

One embodiment comprises a medicament delivery member shield having a diameter that is greater than a shortest distance between the proximal portions of the first leg and the second leg, wherein the longitudinal extension of the first leg and the second leg is longer than the length of the medicament delivery member shield to allow the medicament delivery member shield grippers to engage with a distal end of the medicament delivery member shield when the medicament delivery member shield and gripping member are arranged in the channel of the inner cap structure.

One embodiment comprises a medicament delivery member shield having a diameter that is greater than a shortest distance between the proximal portions of the first leg and the second leg, and having a flexible rubbery external surface, wherein the longitudinal extension of the first leg and the second leg is shorter than the length of the medicament delivery member shield to allow the medicament delivery member shield grippers to engage with the external surface of the medicament delivery member shield when the medicament delivery member shield and the gripping member are arranged in the channel of the inner cap structure.

According to a third aspect of the present disclosure there is provided a method of assembling a medicament delivery device, comprising: a) providing a cap assembly comprising: a cap body having an inner cap structure defining a channel extending along the central axis of the cap body, and configured to receive a medicament delivery member shield, and a gripping member configured to be received in the channel with a friction fit and to receive a medicament delivery member shield, the gripping member having a first leg, a second leg, and a connecting portion extending between the first leg and the second leg, the first leg and the second leg having a respective proximal portion that are radially flexible and extending distally from the connecting portion, each proximal portion having an inclined section extending radially inwards in an axial direction away from the connecting portion, and a respective distal portion extending from the inclined section, the distal portions being radially flexible and extending radially outwards in an axial direction away from the proximal portions to allow the gripping member to receive a medicament delivery member shield between the distal portions, the gripping member and an inner wall of the channel being configured to engage to retain the gripping member in the inner cap structure, and each distal portion being provided with a medicament delivery member shield gripper, b) pushing the gripping member into the channel, with the connecting portion defining the leading edge of the gripping member, until the gripping member engages with the inner wall of the channel, c) placing the cap assembly at a proximal end of a housing of the medicament delivery device, d) placing a medicament container assembly including a medicament delivery member shield into the housing, from a distal end of the housing, e) moving the medicament container assembly in a proximal direction inside the housing until the medicament delivery member shield is received between the first leg, the second leg and the medicament delivery member shield pushes the first leg and the second leg radially outwards, and the medicament delivery member shield grippers engage with the medicament delivery member shield.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

Figure 1:
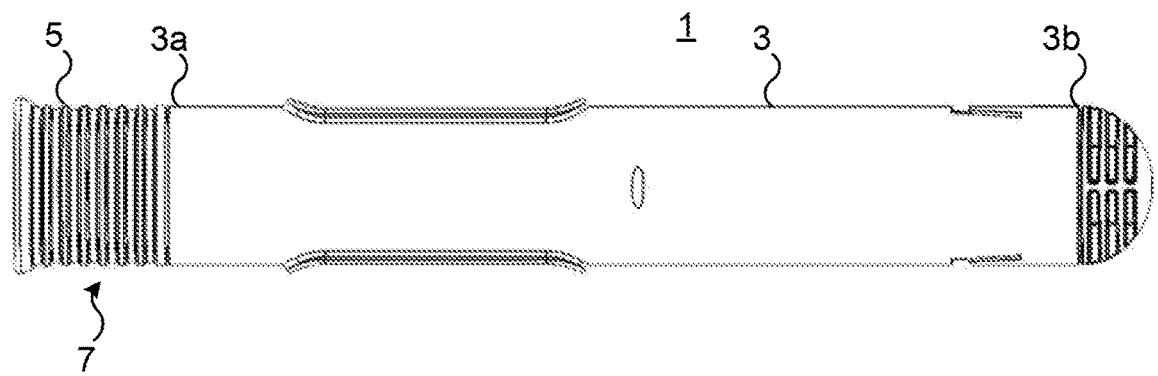
FIG. 1 shows a side view of an example of a medicament delivery device.

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a cap assembly, refers to that end of the cap assembly which, when mounted to a medicament delivery member shield installed on a medicament delivery member in a medicament delivery device, forms the proximal end face of the medicament delivery device. The proximal end of the medicament delivery device is hence that end which is to be pointed towards the site of injection during medicament expulsion. The same considerations also apply when referring to any component of the cap assembly, i.e. the cap body and the gripping member. The "distal end" is the opposite end relative to the proximal end. With "proximal direction" and, equivalently, "proximally" is meant a direction from the distal end towards the proximal end, along the central axis of the cap assembly. With "distal direction" or "distally" is meant the opposite direction to "proximal direction".

The present disclosure relates to a cap assembly for a medicament delivery device. The cap assembly is configured to be mounted to a medicament delivery member shield thereby protecting the medicament delivery member shield and the medicament delivery member. The cap assembly is furthermore configured to engage with the medicament delivery member shield such that removal of the cap assembly from the medicament delivery device removes the medicament delivery member shield from the medicament container prior to medicament administration. The medicament delivery member shield may be made of a rigid material or a flexible/rubbery material. For example, the medicament delivery member shield may be a rigid needle shield or a flexible needle shield.

The cap assembly includes a cap body which when mounted to a medicament delivery member shield installed in a medicament delivery device forms part of a housing assembly enclosing the internal components of the medicament delivery device. Such internal components include the medicament delivery member and a medicament container. To this end, the cap assembly has an external surface forming part of the housing assembly, and an internal structure including an inner cap structure defining a channel extending coaxially with the central longitudinal axis of the cap body, and configured to receive a medicament delivery member shield. The central longitudinal axis of the cap body coincides with the central longitudinal axis of the housing when the cap body is fitted to the main body of the medicament delivery device.

Moreover, the cap assembly includes a longitudinal gripping member configured to receive a medicament delivery member shield and to be received in the channel of the inner cap structure with a friction fit. The longitudinal gripping member has a first leg and a second leg, and a connecting portion which extends between the first leg and the second leg. The connecting portion may be seen as a hub portion of the gripping member.

The radial dimension, or outer diameter, of the connecting portion may essentially correspond to the distance between opposing inner surfaces of the channel, whereby the proximal portions are configured to be received with a friction fit, or a press fit, in the channel.

The first leg and the second leg are arranged opposite to each other and extend longitudinally from the connecting portion in a distal direction, i.e. away from the connecting portion and generally parallel with a central axis of the gripping member. Each of the first leg and the second leg has a proximal portion extending from the connecting portion. Each of the first leg and the second leg also has a distal portion extending from a respective proximal portion.

The proximal portions of the first leg and the second leg are radially flexible and extend towards each other in an axial direction away from the connecting portion, in particular in the distal direction. The proximal portions are hence inclined relative to the central axis of the gripping member, and extend radially inwards in the distal direction.

The distal portions of the first leg and the second leg are radially flexible and extend away from each other in a distal direction. The distal portions thereby form a distal mouth of the gripping member. The configuration of the proximal portions and the distal portions forms a waist of the gripping member.

Each of the two distal portions has a medicament delivery device shield gripper configured to engage with a medicament delivery member shield when the gripping member is arranged in the channel, and the medicament delivery member shield has been received by the gripping member. Due to the dimensioning between the first leg and the second leg, this expands the waist of the gripping member and flexes the distal portions radially inwards. Hereto, the gripping member is designed so that the shortest distance between the first leg and the second leg is smaller than the radial dimension or diameter of the medicament delivery member shield.

Moreover, the gripping member and the inner walls of the channel are configured to engage with each other when the gripping member has been received in a final position in the channel.

A main example of a cap assembly and a medicament delivery device comprising a cap assembly will now be described with reference to FIGS. 1-5*b*.

FIG. 1 shows an example of a medicament delivery device 1, which has not been fully assembled. In particular, the exemplified medicament delivery device 1 has an end cap or end portion which has not yet been mounted.

Medicament delivery device 1 has a housing 3 having a proximal end 3*a* and a distal end 3*b*. The housing 3 is furthermore provided with an inspection window 3*c* enabling a user to inspect medicament contained in a medicament container installed in the medicament delivery device 1.

Medicament delivery device 1 also has a cap assembly 5 including a cap body 7 and a gripping member, not shown in FIG. 1. The cap assembly 5 is configured to be mounted to a medicament delivery member shield arranged inside the housing 3. The cap assembly is thus designed to form a proximal end part of the medicament delivery device 1.

Figure 2:
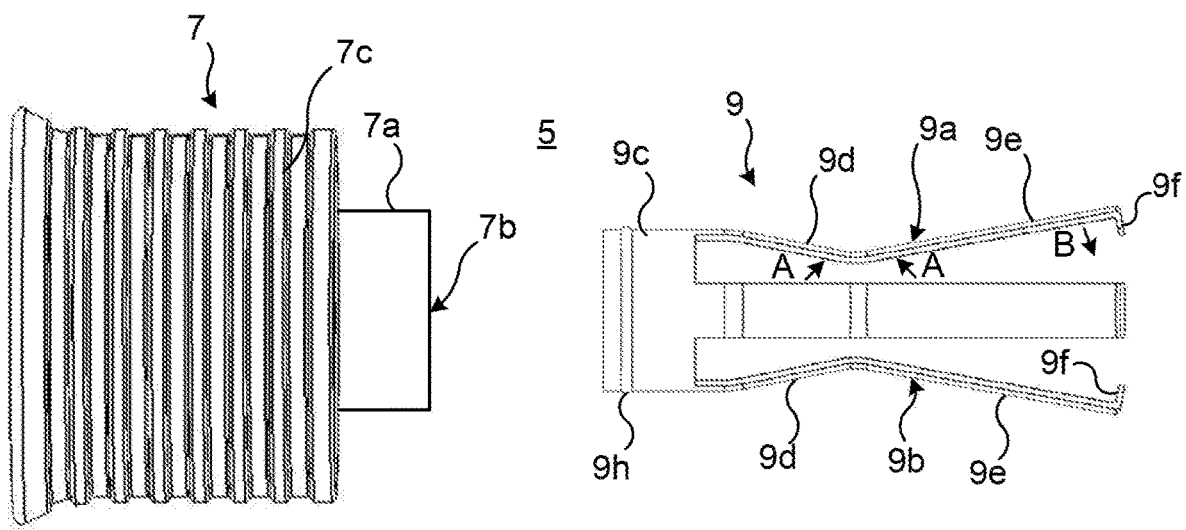
FIG. 2 shows a side view of a cap assembly of the medicament delivery device in FIG. 1.

Turning now to FIG. 2, a side view of the cap assembly 5 is here shown. As mentioned above, the cap assembly 5 includes the cap body 7 and the gripping member 9. The exemplified cap body 7 has an inner and an outer concentrically arranged cylindrical structure. To this end, the cap body 7 has an external surface 7*c* having an essentially cylindrical structure and an inner cap structure 7*a* which also is essentially cylindrical. The inner cap structure 7*a* is hollow and defines a longitudinal channel 7*b* that has a distal end opening. The channel 7*b* is configured to receive the gripping member 9.

The gripping member 9 has a longitudinal body provided with a first leg 9*a*, a second leg 9*b*, and a connecting portion, 9*c*. The connecting portion 9*c* connects the first leg 9*a* and the second leg 9*b*. The connecting portion 9*c* may for example be essentially cylindrical or cylindrical. The first leg 9*a* and the second leg 9*b* extend from the connecting portion 9*c* at about 180 degrees angle apart relative to each other, as seen in the circumferential direction. The first leg 9*a* and the second leg 9*b* are hence arranged opposite to each other.

The connecting portion 9c has a radial protrusion configured to engage with a corresponding recess in the inner wall of the channel 7b. According to the example shown in FIG. 2, the radial protrusion is a circumferential flange 9h extending along the external surface of the connecting portion 9c. The circumferential flange 9h is configured to engage with a corresponding circumferential recess of the inner wall of the channel 7b. The gripping member 9 can thereby engage with the inner cap structure 7a and retain its position inside the channel 7b after the gripping member 9 has been assembled with the cap body 7.

Each of the first leg 9a and the second leg 9b has a respective proximal portion 9d extending longitudinally in the distal direction from the connecting portion 9c. The proximal portions 9d extend towards each other in the distal direction. The radial distance between the proximal portion 9d thus decreases in the distal direction. Each proximal portion 9d hence has an inclined section or portion. The shortest distance between the proximal portions 9e of the first leg 9a and the second leg 9b is smaller than the diameter or radial dimension of that portion of the medicament delivery member shield which is to be received between the proximal portions 9d. According to the example, the location of the shortest distance is in a transition portion of each of the first leg 9a and the second leg 9b, where the inclination changes from radially inwards towards radially outwards in the distal direction, i.e. a distal portion 9e. As defined herein, this transition portion forms part of the proximal portion 9d.

Each of the first leg 9a and the second leg 9b also has a respective distal portion 9e. Each distal portion 9e extends from a respective proximal portion 9d, in particular from a respective inclined section. The distal portions 9e extend radially outwards, in the distal direction. The radial distance between the oppositely arranged distal portions 9e hence increases in the distal direction. The distal portions 9e form a distal mouth of the gripping member 9, allowing the gripping member 9 to receive a medicament delivery member shield between the first leg 9a and the second leg 9b. Moreover, the configuration of the proximal portions 9d and the distal portions 9e forms a waist-like shape of the gripping member 9.

Each distal portion 9e is provided with a respective medicament delivery member shield gripper 9f. According to the present example, the distal end of each distal portion 9e is provided with the medicament delivery member shield grippers 9f. In the present variation, the medicament delivery member shield grippers 9f extend radially inwards. In the exemplified gripping member 9, the distal portions 9e extending between the proximal ends 9d and the medicament delivery member shield grippers 9f are inclined with respect to the central axis of the gripping member 9, and essentially straight, i.e. non-curved. Each proximal portion 9d may also extend in an inclined manner relative to the central axis of the gripping member, and essentially straight, between the connecting portion 9c and the transition portion.

The first leg 9a and the second leg 9b are radially flexible or elastic. In particular, both the proximal portions 9e and the distal portions 9e are radially flexible or elastic, so that when sufficiently large radial outwards-pointing forces act on the first leg 9a and the second leg 9b, in particular by a medicament delivery member shield being received therebetween, the inclination of both the first portions 9d and the second portions 9e is leveled out or reduced, as illustrated by arrows A. The distal ends of the distal portions 9e, and thus the medicament delivery member shield grippers 9f, are thereby displaced radially inwards as shown by arrow B, in case the gripping member 9 is arranged in channel 7b. The medicament delivery member shield grippers 9f may thereby engage with the medicament delivery member shield.

Although not fully visible, the exemplified gripping member 9 has four legs for reasons of symmetry. Alternatively, the gripping member could be provided with only two legs arranged oppositely relative to each other. There could also be more than four legs, in theory generally any integer number that is evenly divisible with the integer two for symmetry, or even odd number of legs if the legs are evenly spaced.

Figure 3:
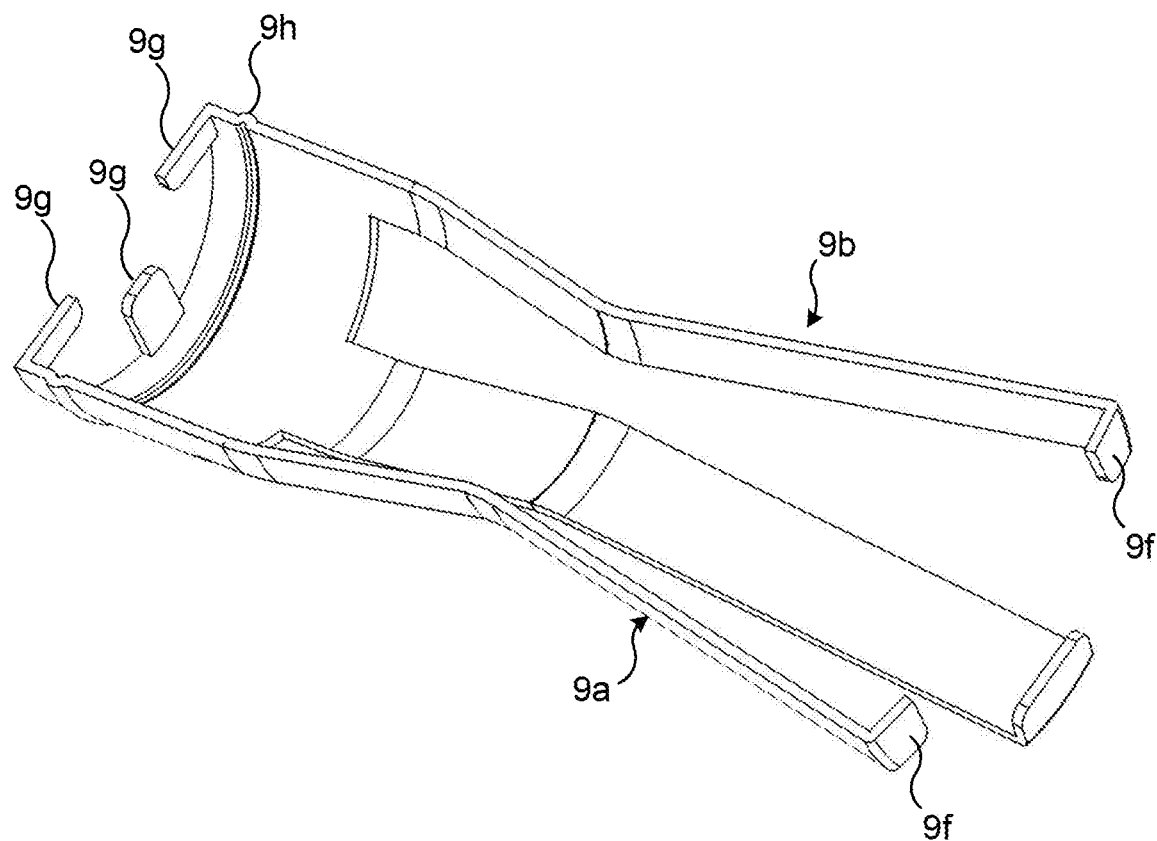
FIG. 3 is a perspective view of a gripping member having been subjected to a longitudinal section.

The connecting portion 9c may optionally also be provided with radial support structures 9g, as shown in FIG. 3. The radial support structures 9g extend radially inwards towards the central axis of the gripping member 9. The radial support structures 9g are configured to prevent a medicament delivery member shield from sliding past the proximal end of the gripping member 9, in the proximal direction, when pushed into the gripping member 9.

The gripping member 9 may for example be made of metal, such as steel or aluminium, or a plastic material.

Figure 4:
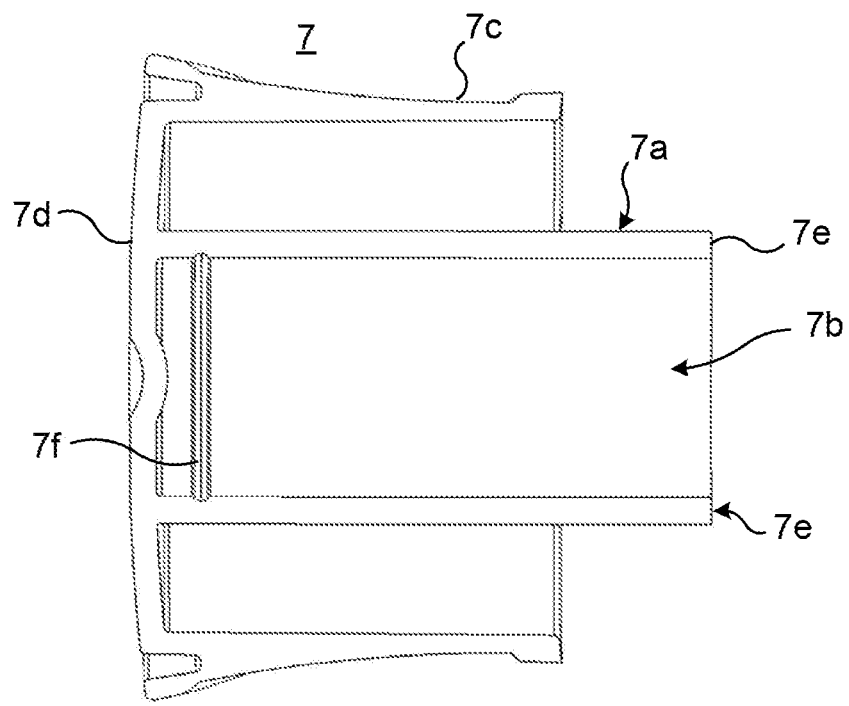
FIG. 4 is a longitudinal section of an example of a cap body of a cap assembly.

FIG. 4 depicts a longitudinal section of cap body 7. According to the example in FIG. 4, cap body 7 has an external surface 7c which forms part of the external surface of the housing assembly that also includes the housing 3, of the medicament delivery device 1, for protecting internal components thereof. As previously mentioned, the inner cap structure 7b is coaxial with and concentrically arranged with the external surface 7c of the cap body 7. The inner cap structure 7b forms an essentially cylindrical channel 7b having a distal end opening for receiving the gripping member 9 and a medicament delivery member shield received between the first leg 9a and the second leg 9b of the gripping member 9. It is the engagement between the gripping member 9 and the medicament delivery member shield that retain the cap body 7 in a mounted state in which it forms part of the housing assembly.

The cap body 7 has a recess, which according to the present example is a circumferential groove 7f that extends along the inner surface of the channel 7a. The circumferential groove 7f is configured to engage with the circumferential flange 9h of the gripping member 9. The circumferential groove 7f is arranged in a proximal portion of the channel 7b thereby enabling engagement with the connecting portion 9c, which forms the leading edge of the gripping member 9, when pushed into the channel 7b. In this manner, a majority of the gripping member 9 may be received in the channel 7b before the gripping member 9 and the cap body 7 engage with each other, and preventing the gripping member 9 from being axially displaced relative to the cap body 7.

The cap body 7 has a proximal end 7d with a radial surface which according to the present example is closed in the sense that in a mounted state it forms a closed front wall of the medicament delivery device 1. The cap body 7 also has a distal end 7e which according to the example is formed by the distal end of the inner cap structure 7b. According to the example, the longitudinal extension of the inner cap structure 7b is greater than the longitudinal extension of the external surface 7c of the cap structure 7. The cap body 7 may thereby receive a greater portion of a medicament delivery member shield, for a more secure fit or engagement therewith.

Figure 5A:
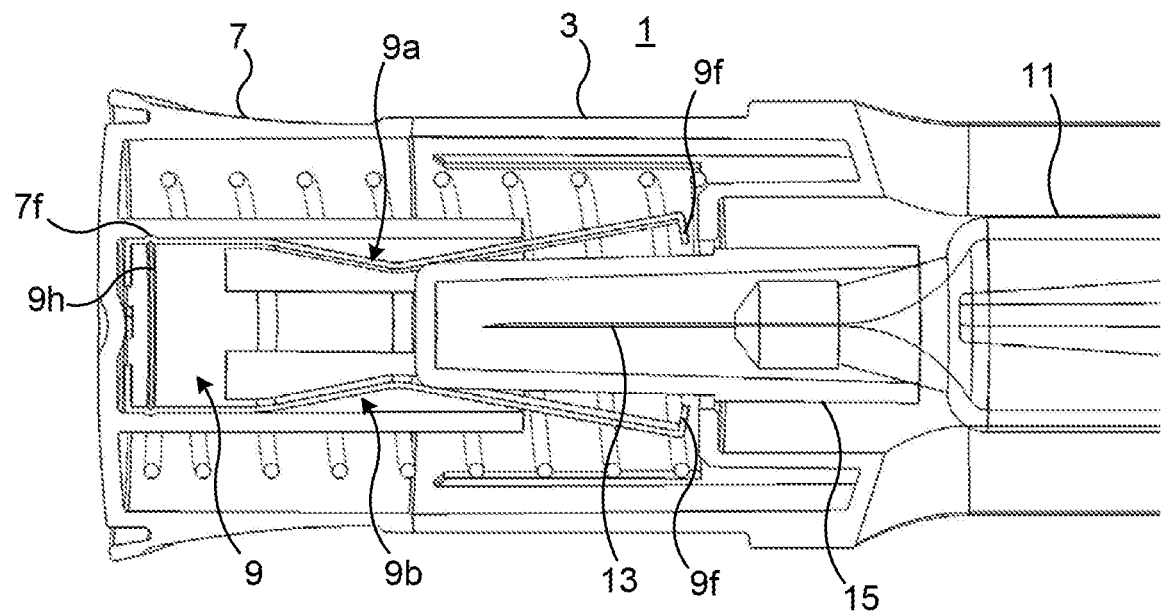
FIG. 5a is a longitudinal section of a proximal portion of the medicament delivery device in FIG. 1 during assembly of a medicament delivery member shield and the cap assembly.
Figure 5B:
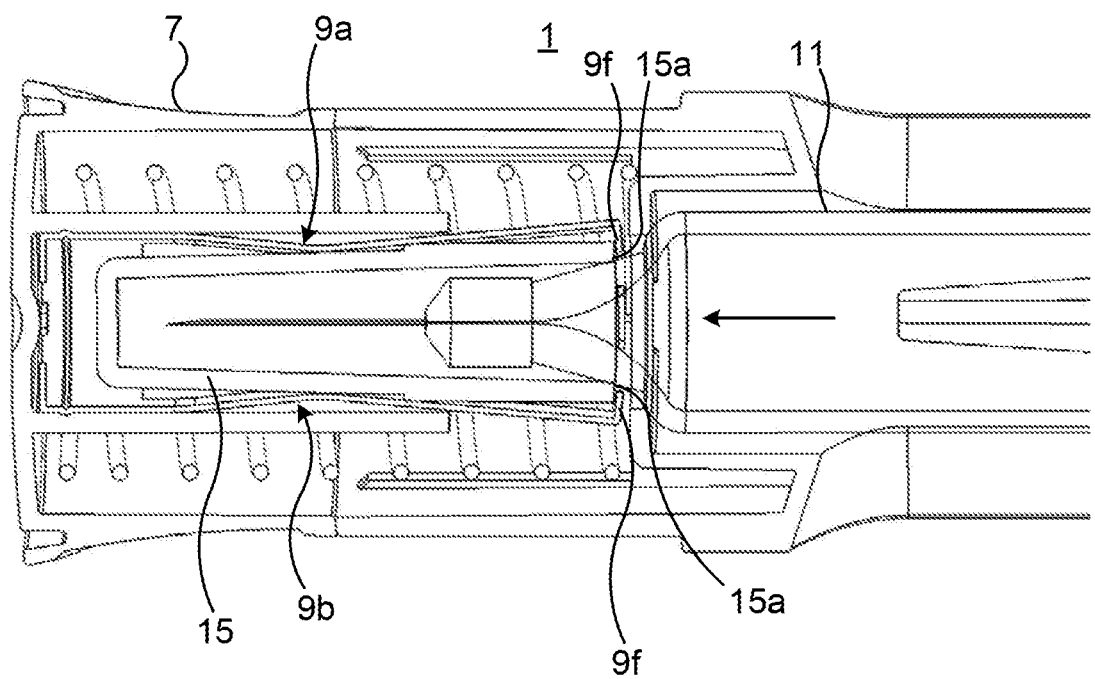
FIG. 5b is a longitudinal section of a proximal portion of the medicament delivery device in FIG. 1 when the medicament delivery member shield has been assembled with the cap assembly.

With reference to FIGS. 5a-5b the cap assembly 5 will now be shown during assembly of a medicament delivery device 1.

During assembly, the gripping member 9 is provided into channel 7b of the inner cap structure 7a, with the connecting portion 9c forming the leading edge of the gripping member 9 when being placed in the channel 7b. The gripping member 9 engages with the inner wall of the channel 7b when it reaches its final position in the channel 7b. This procedure of the cap assembly 5 has already been performed prior to the assembly stages described below.

According to the example in FIG. 5a, the medicament delivery device 1 is an injector, and the medicament delivery member is a needle 13. An arrangement comprising a medicament container 11, a needle 13, and a medicament delivery member shield 15 protecting the needle 13, both of which are mounted onto the medicament container 11, is advantageously inserted from a distal end opening in the housing 3 at this stage and moved proximally within the housing 3.

In FIG. 5a the medicament delivery member shield 15 has not yet been fully received by the channel 7b or by the gripping member 9. The proximal portions 9d of the first leg 9a and the second leg 9b are in their default position, extending radially inwards in the distal direction. The shortest distance between the proximal portions 9d, i.e. the transition portions, is less than a diameter of a portion of the medicament delivery member shield 15 that will pass by these transition portions when pushed further into the gripping member 9 and the channel 7b.

The distal portion 9e of each of the first leg 9a and the second leg 9b extends radially outwards in the distal direction, which is the default state of the gripping member 9.

In FIG. 5b, the medicament delivery member shield 15 has been maximally received into the channel 7b of the inner cap structure 7a and the gripping member 9. With "maximally received" is here meant that the medicament delivery member shield 15 has been received into a final assembly position in the channel 7b and the gripping member 9. This position is achieved by moving the medicament container 11 further in the proximal direction within the housing 3, i.e. to the left in FIG. 5b as shown by the arrow. The outer surface of the medicament delivery member shield 15 pushes the first leg 9a and the second leg 9b radially outwards, away from each other, as the medicament delivery member shield 15 enters the "waist area" of the gripping member 9. Since the inner wall of the channel 7b limits radial displacement of the first leg 9a and the second leg 9b, the inclination of both the proximal portions 9d and the distal portions 9e will be reduced. The shortest distance between proximal portions 9d will therefore increase, allowing the medicament delivery member shield 15 to pass therebetween. The distal portions 9e will thereby bend radially inwards. The medicament delivery member shield grippers 9f will therefore move radially inwards to engage with the medicament delivery member shield 15. As per the present example, the axial length of the gripping member 9 is greater than that of the medicament delivery member shield 15, which is thereby fully received by the gripping member 9. The medicament delivery member shield grippers 9f extend beyond the distal edge 15a of the medicament delivery member shield 15. Moreover, the medicament delivery member shield grippers 9f extend radially inwards beyond the outer diameter of the medicament delivery member shield 15 so that the medicament delivery member shield grippers 9f can engage with the distal edge 15a or distal end of the medicament delivery member shield 15 when the cap body 7 is pulled off, i.e. removed. It should however be noted, that as an alternative to the illustrated example, the medicament delivery member grippers could be configured to grip into the external surface of the medicament delivery member shield in case the medicament delivery member shield 15 is made of a rubbery or flexible material, and the gripping member is made shorter longitudinally than the longitudinal extension of the medicament delivery member shield.

When the cap body 7 is pulled off the medicament delivery device 1 the medicament delivery member shield grippers 9f engage with the distal edge 15a of the medicament delivery member shield 15. Due to the fixed position of the gripping member 9 in the channel 7b, the gripping member 9 will pull the medicament delivery member shield off the medicament container 11 to thereby eventually expose the needle 13 when the cap body 7 has been fully removed from the remainder of the medicament delivery device 1.

The medicament delivery device utilising the cap assembly according to the present invention may for example be a manual injector, an auto-injector, an inhaler, or an eye dispenser.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A gripping member for removing a medicament delivery member shield of a medicament delivery device, the gripping member comprising:
   a connecting portion;
   a first leg comprising (i) a first proximal portion that extends distally and radially inward from the connecting portion and (ii) a first distal portion that extends distally and radially outward from the first proximal portion; and
   a second leg comprising (i) a second proximal portion that extends
   distally and radially inward from the connecting portion and (ii) a second distal portion that extends distally and radially outward from the second proximal portion,
   wherein the first leg and the second leg are configured to engage the medicament delivery member shield of the medicament delivery device.

2. The gripping member of claim 1, further comprising a radial protrusion that extends radially outward from the connecting portion.

3. The gripping member of claim 2, wherein the radial protrusion encircles a circumference of the connecting portion.

4. The gripping member of claim 2, wherein the radial protrusion is separated from a proximal end of the connecting portion.

5. The gripping member of claim 1, further comprising a radial support structure that extends radially inward from the connecting portion.

6. The gripping member of claim 5, wherein the radial support structure is located at a proximal end of the connecting portion.

7. The gripping member of claim 5, wherein the radial support structure is configured to prevent proximal movement of the medicament delivery member shield past the radial support structure.

8. The gripping member of claim 1, wherein the gripping member is formed of metal.

9. The gripping member of claim 1, wherein the gripping member is formed of steel.

10. The gripping member of claim 1, wherein the gripping member is formed of aluminum.

11. The gripping member of claim 1, wherein the gripping member is formed of plastic.

12. The gripping member of claim 1, further comprising a first gripper that extends distally and radially inward from the first distal portion and a second gripper that extends distally and radially inward from the second distal portion.

13. A cap assembly comprising:
the gripping member of claim 1, wherein a first junction of the first proximal portion and the first distal portion and a second junction of the second proximal portion and the second distal portion form a concave waist area of the gripping member; and
a cap body configured to receive the connecting portion, wherein
insertion of a medicament delivery shield into the gripping member causes the concave waist area to radially expand when the connecting portion is received within the cap body.

14. The cap assembly of claim 13, wherein the cap body comprises a cylindrical channel that is configured to receive the connecting portion.

15. The cap assembly of claim 13, wherein the first leg and the second leg extend distally beyond the medicament delivery shield when the medicament delivery shield is inserted into the gripping member.

16. The cap assembly of claim 13, wherein insertion of the medicament delivery shield between the first leg and the second leg causes a distal end of the first distal portion and a distal end of the second distal portion to move radially toward each other.

17. The cap assembly of claim 13, wherein insertion of the medicament delivery shield between the first leg and the second leg causes a distal end of the first proximal portion and a distal end of the second proximal portion to move radially away each other.

18. The cap assembly of claim 13, the gripping member further comprising a radial protrusion that extends radially outward from the connecting portion, the cap body comprising a radial recess that is configured to mate with the radial protrusion to secure the connecting portion within the cap body.

19. The cap assembly of claim 13, wherein the concave waist area is inside the cap body when the connecting portion is inserted into the cap body.

20. A method of coupling the cap assembly of claim 13 to the medicament delivery member shield, the method comprising:
inserting the connecting portion into the cap body such that the first leg and the second leg extend distally beyond the cap body;
moving the first leg and the second leg into the medicament delivery device such that a proximal end of the medicament delivery member shield is inserted between the first distal portion and the second distal portion;
moving the proximal end of the medicament delivery member shield proximally through the concave waist area, causing the concave waist area to expand outwardly; and
moving the proximal end of the medicament delivery member shield proximally such that the first leg and the second leg engage a distal end of the medicament delivery member shield.

* * * * *